(12) United States Patent
Shimomura et al.

(10) Patent No.: US 7,642,274 B2
(45) Date of Patent: *Jan. 5, 2010

(54) INHIBITOR OF PAIN THRESHOLD DECREASE

(75) Inventors: Kyoichi Shimomura, Ikoma (JP); Hiroyuki Aono, Ikoma (JP); Yaeko Tsukahara, Ikoma (JP); Taeko Hata, Kaizuka (JP)

(73) Assignee: Santen Pharmaceutical Co., Ltd., Osaka-shi, Osaka (JP)

( * ) Notice: Subject to any disclaimer, the term of this patent is extended or adjusted under 35 U.S.C. 154(b) by 546 days.

This patent is subject to a terminal disclaimer.

(21) Appl. No.: 10/562,742

(22) PCT Filed: Jul. 2, 2004

(86) PCT No.: PCT/JP2004/009766

§ 371 (c)(1),
(2), (4) Date: Dec. 29, 2005

(87) PCT Pub. No.: WO2005/002622

PCT Pub. Date: Jan. 13, 2005

(65) Prior Publication Data

US 2007/0117853 A1 May 24, 2007

(30) Foreign Application Priority Data

Jul. 4, 2003 (JP) .............................. 2003-270967

(51) Int. Cl.
*A01N 43/78* (2006.01)
*A61K 31/425* (2006.01)
*A01N 43/40* (2006.01)
*A61K 31/445* (2006.01)
*A61K 31/44* (2006.01)
*C07D 417/00* (2006.01)
*C07D 413/00* (2006.01)
*C07D 419/00* (2006.01)
*C07D 261/20* (2006.01)

(52) U.S. Cl. ...................... 514/367; 514/321; 514/342; 544/135; 544/368; 546/198

(58) Field of Classification Search .................. 514/342, 514/321, 367; 544/135, 368; 546/198, 280
See application file for complete search history.

(56) References Cited

U.S. PATENT DOCUMENTS 4,547,513 A 10/1985 Iwao et al.
5,646,151 A 7/1997 Kruse et al.
5,776,972 A 7/1998 Barber et al.
6,303,611 B1 * 10/2001 Zhang et al. ............ 514/252.11
7,410,987 B2 * 8/2008 Tokai et al. .................. 514/367
2001/0051181 A1 12/2001 Van Osdol et al.

FOREIGN PATENT DOCUMENTS

| EP | 1 496 053 A1 | 1/2005 |
|---|---|---|
| JP | 60-139679 A | 7/1985 |
| JP | 62-221680 A | 9/1987 |
| JP | 9-20659 A | 1/1997 |
| JP | 9-020659 A | 1/1997 |
| JP | 2002-52444 A | 8/2002 |
| JP | 2002-524444 A | 8/2002 |
| JP | 2004-002352 A | 1/2004 |
| JP | 2004-2352 A | 1/2004 |
| WO | WO 00/14065 A1 | 3/2000 |

OTHER PUBLICATIONS

H. Ohara et al, "Mechanism of Hyperalgesia in SART Stressed (Repeated Cold Stress Mice: Antinociceptive Effect of Neurotropin", *Japan, J. Pharmacol.*, 57, pp. 243-250 (1991).
H. Vanegas et al, "Effects of antagoinists to high-threshold calcium channels upon spinal mechanisms of pain, hyperalgesia and allodynia", *PAIN*, 85, pp. 9-18 (2000).
K.K. Mikusu, *Opioid No Subete*, pp. 25-36 (1999).
K.K. Mikusu, *Opioid No Subete*, pp. 213-232 (1999).
K.K. Mikusu, *Opioid Chiryo*, pp. 246-253 (2000).
Omiya et al., "Changes in Analgesia-Producing Mechanism of Repeated Cold Stress Loading in Mice," *Pharmacology Biochemistry and Behavior*, vol. 65, No. 2, Feb. 2000, pp. 261-266.
Janice Ho et al., "Putative kappa-2 Opioid Agonists Are Antihyperalgesic in a Rat Model of Inflammation," *The Journal of Pharmacology and Experimental Therapeutics*, (1997), vol. 281, No. 1, pp. 136 to 141.
M.C. Holden Ko et al., "Local Administration of mu or kappa opioid agonists attenuates capsaicin-induced thermal hyperalgesia via peripheral opioid receptors in rats," *Psychopharmacology*, 2000, vol. 148, No. 2, pp. 180 to 185.
Horacio Vanegas et al., "Effects of antagonists to high-threshold calcium channels upon spinal mechanisms of pain, hyperalgesia and allodynia," *Pain*, (2000), vol. 85, pp. 9 to 18.
Supplementary European Search Report for EP 04747234.5/1642590, Apr. 15, 2009; Applicant: Santen Pharmaceutical Co., Ltd.
Japanese Patent Office Action entitled "Notice of Reasons for Rejection" dated Apr. 21, 2009 for application No. JP 2004-196146A.

* cited by examiner

*Primary Examiner*—Sreeni Padmanabhan
*Assistant Examiner*—Samira Jean-Louis
(74) *Attorney, Agent, or Firm*—Frishauf, Holtz, Goodman & Chick, P.C.

(57) ABSTRACT

The invention aims to provide a drug having an activity on inhibiting a decrease in pain threshold. Since a κ-opioid receptor agonist effectively inhibits the decrease in pain threshold, it is useful as an inhibitor of pain threshold decrease.

7 Claims, 1 Drawing Sheet

INHIBITOR OF PAIN THRESHOLD DECREASE

This application is the United States national phase application of International Application PCT/JP2004/009766 filed Jul. 2, 2004.

TECHNICAL FIELD

The present invention relates to an inhibitor of pain threshold decrease comprising a κ-opioid receptor agonist as an active ingredient.

BACKGROUND ART

As an opioid receptor, three opioid receptors, μ-, κ- and δ-opioid receptors have been known (K. K. Mikusu, Opioid no Subete, 25-36 (1999)). The μ-opioid receptor is distributed in the cerebral cortex, amygdaloid nucleus and the like, and main agonists are morphine, codeine and the like. The κ-opioid receptor is distributed in the hypothalamus, spinal cord and the like, and its agonists are ketocyclazocine and the like. The δ-opioid receptor is distributed in the extrapyramidal system, and its agonists are enkephalin and the like. The μ-opioid receptor agonist typified by morphine and codeine has an excellent analgesic activity, but its dependence on the body and mind is strong, and it involves side effects such as complication of constipation.

Meanwhile, the κ-opioid receptor agonist is characterized in that it does not exhibit dependence unlike morphine, and trans-2-(3,4-dichlorophenyl)-N-methyl-N-[2-(1-pyrrolidinyl)cyclohexyl]acetamide (U-50488), 2,2-diphenyl-N-[2-(3-(S)-hydroxy-1-pyrrolidinyl)-1-(S)-phenylethyl]Methylacetamide (Asimadoline) and the like are known (K. K. Mikusu, "Opioid no Subete", 25-36 (1999), K. K. Mikusu, "Opioid no Subete", 213-232 (1999)).

Pain is roughly classified into acute pain and chronic pain. The acute pain is pain accompanied by tissue disorders, and causal association with tissue disorders is clear. Meanwhile, the chronic pain is pain which continues even after curing tissue disorders, and no clear organic cause has been found out. However, it has been reported that a plastic change of a descending inhibition system participates in development of the chronic pain (K. K. Mikusu, "Opioid Chiryo", 246-253 (2000)). When pain is prolonged, a pain threshold is gradually decreased, and pain is felt also due to an action, a tactile sense or the like which has not given a feel of pain. The pain threshold here referred to indicates a sensitivity of pain. More specifically, it indicates the minimum level of stimulation which gives a feel of pain.

Accordingly, the decrease in pain threshold increases the sensitivity of pain, and amplifies the same. Therefore, when the decrease in pain threshold can be inhibited, it is possible to effectively treat the chronic pain. Japan J. Pharmacol., 57, 243-250 (1991) reports that neurotropin, an agent for treating chronic pain can inhibit a decrease in pain threshold by activating a descending inhibition system. However, its chronic pain-inhibiting effect is not necessarily satisfactory.

DISCLOSURE OF THE INVENTION

As stated above, a therapeutic agent effective for treating chronic pain can be provided by searching a drug for inhibiting a decrease in pain threshold.

The present inventors conducted a test for inhibiting a decrease in pain threshold based on repetitive cold stress models on various κ-opioid receptor agonists. They have then found that all of κ-opioid receptor agonists have an excellent activity on inhibiting a decrease in pain threshold. Accordingly, the κ-opioid receptor agonists can radically improve the: chronic pain caused by the decrease in pain threshold. The repetitive cold stress model which is one of chronic pain models is based on the fact that a decrease in function of a descending inhibition system induces a decrease in pain threshold.

The present invention is an inhibitor of pain threshold decrease comprising a κ-opioid receptor agonist as an active ingredient, and this inhibitor is characterized in that it is greatly effective for treating chronic pain in particular.

The κ-opioid receptor agonist of the invention is not particularly limited, and is exemplified by compounds described in JP-A-2004-2352 and arylacetic acid (N-alkyl-N-(N',N'-dialkyl)aminoalkyl)amide derivatives. These κ-opioid receptor agonists have an excellent activity on inhibiting a decrease in pain threshold as will be described in detail under the item "Pharmacological Test".

JP-A-2004-2352 discloses compounds represented by the following formula or salts thereof.

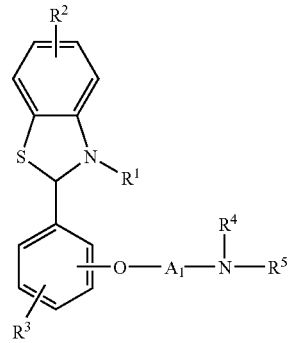

wherein $R^1$ represents an acyl group;
$R^2$ and $R^3$, which are the same or different, represent a hydrogen atom, a halogen atom, an alkyl group, a cycloalkyl group, an aryl group, a hydroxyl group or its ester, an alkoxy group, an aryloxy group, a carboxy group or its ester, an alkylcarbonyl group, an arylcarbonyl group, an amino group, an alkylamino group, an arylamino group, a cyano group or a nitro group, the alkyl group, the cycloalkyl group, the aryl group, the alkoxy group, the aryloxy group, the alkylcarbonyl group, the arylcarbonyl group, the alkylamino group or the arylamino group can be substituted with a halogen atom, an alkyl-group, a cycloalkyl group, an aryl group, a hydroxyl group or its ester, an alkoxy group, an aryloxy group, a carboxy group or its ester, an alkylcarbonyl group, an arylcarbonyl group, an amino group, an alkylamino group, an arylamino group, a cyano group or a nitro group;
$R^4$ and $R^5$, which are the same or different, represent a hydrogen atom, an alkyl group, a cycloalkyl group, an aryl group, a hydroxyl group or its ester, an alkoxy group, an aryloxy group or an acyl group, the alkyl group, the cycloalkyl group, the aryl group, the alkoxy group, the aryloxy group or the acyl group can be substituted with a halogen atom, an alkyl group, a cycloalkyl group, an aryl group, a hydroxyl group or its ester, an alkoxy group, an aryloxy group, a carboxy group or its ester, an alkylcarbonyl group, an arylcarbonyl group, an amino group, an alkylamino group, an arylamino group, a mercapto group, an alkylthio group, an arylthio group, a cyano group, a nitro group or a heterocycle, and further the alkyl group, the cycloalkyl group, the aryl group, the alkoxy group, the aryloxy group, the alkylcarbonyl group, the arylcarbonyl group, the alkylamino group, the arylamino group, the alkylthio group, the arylthio group or the heterocycle can be substituted with an aryl group, a hydroxyl group or its ester, an alkoxy group, an aryloxy group, an alkoxyalkoxy group, a carboxy group or its ester;

$R^4$ and $R^5$ can be bound to form a heterocycle, the heterocycle can be substituted with a halogen atom, an alkyl group, a cycloalkyl group, an aryl group, a hydroxyl group or its ester, an alkoxy group, an aryloxy group, a carboxy group or its ester, and further the alkyl group, the cycloalkyl group, the aryl group, the alkoxy group or the aryloxy group can be substituted with an aryl group, a hydroxyl group or its ester, an alkoxy group, an aryloxy group, an alkoxyalkoxy group, a carboxy group or its ester; and $A_1$ represents an alkylene group.

Examples of the compounds represented by the general formula include 3-acetyl-6-chloro-2-[2-(3-(N-(2-hydroxyethyl)-N-isopropylamino)propoxy)-5-methoxyphenyl]benzothiazoline, 3-acetyl-6-chloro-2-[2-(3-(N-hydroxy-N-isopropylamino)propoxy)-5-methoxyphenyl]benzothiazoline, 3-acetyl-6-chloro-2-[2-(3-(N-isopropyl-N-(2-methoxyethyl)amino)propoxy)-5-methoxyphenyl]benzothiazoline, 3-acetyl-6-chloro-2-[2-(3-(N-(2-ethoxyethyl)-N-isopropylamino)propoxy)-5-methoxyphenyl]benzothiazoline, 3-acetyl-5-chloro-2-[2-(3-(N-(2-hydroxyethyl)-N-isopropylamino)propoxy)-5-methoxyphenyl]benzothiazoline, 3-acetyl-6-chloro-2-[2-(3-(N-(2hydroxyethyl)-N-isopropylamino)-1-methylpropoxy)-5-methoxyphenyl]benzothiazoline, 3-acetyl-2-[2-(3-(N-(2-ethoxyethyl)-N-isopropylamino)propoxy)-5-methoxyphenyl]benzothiazoline, 3-acetyl-6-chloro-2-[2-(3-(N-(2-methoxyethyl)-N-isopropylamino)propoxy)-5-methoxyphenyl]benzothiazoline, 3-acetyl-6-chloro-2-[2-(3-(N-isopropyl-(N-methoxymethyloxyethyl)amino)propoxy)-5-methoxyphenyl]benzothiazoline, 3-acetyl-6-chloro-2-[2-(3-(N-isopropyl-N-(2-(2-methoxyethoxymethoxy)ethyl)amino)propoxy)-5-methoxyphenyl]benzothiazoline, 2-[2-(3-(N-(2-acetoxyethyl)-N-isopropylamino)propoxy)-5-methoxyphenyl]-3-acetyl-6-chlorobenzothiazoline, 3-acetyl-6-chloro-2-[2-(3-(N-isopropyl-N-phenylcarboxyethylamino)propoxy)-5-methoxyphenyl]benzothiazoline and the like.

Preferred compounds are

3-Acetyl-6-chloro-2-[2-(3-(N-(2-hydroxyethyl)-N-isopropylamino)propoxy)-5-methoxyphenyl]benzothiazoline, 3-acetyl-6-chloro-2-[2-(3-(N-(2-methoxyethyl)-N-isopropylamino)propoxy)-5-methoxyphenyl]benzothiazoline, 3-acetyl-6-chloro-2-[2-(3-(N-(2-ethoxyethyl)-N-isopropylamino)propoxy)-5-methoxyphenyl]benzothiazoline, 3-acetyl-6-chloro-2-[2-(3-chloropropoxy)-5-methoxyphenyl]benzothiazoline, 3-acetyl-6-chloro-2-[2-(3-(N-(2-hydroxyethyl)-N-isopropylamino)-1-methylpropoxy)-5-methoxyphenyl]benzothiazoline, 2-[2-(3-(N-(2-acetoxyethyl)-N-isopropylamino)propoxy)-5-methoxyphenyl]-3-acetyl-6-chlorobenzothiazoline or 3-acetyl-6-chloro-2-[2-(3-(N-isopropyl-(N-methoxymethyloxyethyl)amino)propoxy)-5-methoxyphenyl]benzothiazoline.

As arylacetic acid (N-alkyl-N-(N',N'-dialkyl)aminoalkyl) amide derivatives, compounds having a common structure of phenylacetic acid (N-methyl-N-pyrrolidinylethyl)amide or salts thereof described in K. K. Mikusu, "Opioid no Subete", 213-232 (1999) are preferable. The κ-opioid receptor agonist can be compounds other than arylacetic acid (N-alkyl-N-(N', N'-dialkyl)aminoalkyl)amide derivatives.

Specific examples of these compounds include U-50488 (trans-2-(3,4-dichlorophenyl)-N-methyl-N-[2-(1-pyrrolidinyl)cyclohexyl]acetamide), PD-117302, Spiradoline (2-(3,4-dichlorophenyl)-N-methyl-N-[(5R*,7S*,8S*)-7-(1-pyrrolidinyl)-1-oxaspiro[4,5]deca-8-yl]acetamide), Enadoline (N-methyl-N-[(5R,7S,8S)-7-(1-pyrrolidinyl)-1-oxaspiro[4,5]deca-8-yl]-4-benzofuranacetamide hydrochloride), HN-11608, BRL-52656 (S(−)-2-(1-pyrrolidinylmethyl)-1-(4-trifluoromethylphenyl)acetylpiperidine hydrochloride), BRL-53001 ((2S)-1-(1-oxo-3,4-dihydro-(2H)-naphto-6-yl)acetyl-2-dimethylaminomethylpiperidine hydrochloride), BRL-53114 ((−)-1-(4-trifluoromethylphenyl)acetyl-2-(1-pyrrolidinyl)-3,3-dimethylpiperidine hydrochloride), BRL-52537, BRL-52580, BRL-52974, GR-89696 (4-[3,4-dichlorophenyl)acetyl]-3-(1-pyrrolidinylmethyl)-1-piperazinecarboxylic acid methyl ester), GR-107537 ([S-(R*,R*)]-5-[(3,4-dichlorophenyl)acetyl]-4,5,6,7-tetrahydro-4-[(3-hydroxy-1-pyrrolidinyl)methyl]furo(3,2-c]pyridine), GR-44821 (1-[3,4-dichlorophenyl)acetyl]-2-[(3-oxy-1-pyrrolidinyl)methyl]piperidine(Z)-2-butenedioate (1:1)), GR-102908, GR-94839, GR-45809, GR-91272 (5-[3,4-dichlorophenyl)acetyl]-4,5,6,7-tetrahydro-4-[(3-hydroxy-1-pyrrolidinyl)methyl]furo[3,2-c]pyridine monohydrochloride), GR-129083, GR-103545, GR-38414, GR-86014, R-84760 ((3R)-4-[(1S)-5,6-dichloro-2,3-dihydro-1H-inden-1-yl]carbonyl]-3-(1-pyrrolidinylmethyl)thiomorpholine monohydrochloride), Niravoline (N-methyl-2-(m-nitrophenyl)-N-[(1S,2S)-2-(1-pyrrolidinyl)-1-indanyl]acetamide), Ocfentanil (2'-fluoro-2-methoxy-N-(1-phenetyl)-4-piperidyl)acetanilide monohydrochloride), Dup-747 (trans (+,−)-3,4-dichloro-N-methyl-N-[1,2,3,4-tetrahydro-5-methoxy-2-(1-pyrrolidinyl)-1-naphthalenyl]benzeneacetamide), ICI-199441, ICI-204448 ((+,−)-[3-[1-[[(3,4-dichlorophenyl)acetyl]methylamino]-2-(1-pyrrolidinyl)ethyl]phenoxy]acetic acid monohydrochloride), ICI-197067 ((S)-3,4-dichloro-N-methyl-N-[2-methyl-1-(1-pyrrolidinylmethyl)propyl]benzeneacetamide monohydrochloride), Fedotozine ((+)-(R)-α-ethyl-N,N-dimethyl-α-[[(3,4,5-trimethoxybenzyl)oxy]methylbenzylamine), Asimadoline (2,2-diphenyl-N-[2-(3-(S)-hydroxy-1-pyrrolidinyl)-1-(S)-phenylethyl]methylacetamide), ADL-10-0101, ADL-10-0116, ADL-10-0398, ADL-01-0215, ADL-10-386, CJ-15161 (4-[[(1S)-2-[(3S)-3-hydroxy-1-pyrrolidinyl]-1-phenylethyl]methylamino-N-propylbenzamide]), CJC-1008, EN-3231, Xorphanol (17-(cyclobutylmethyl)-8β-methyl-6-methylenemorphinan-3-ol)methanesulfonic acid salt, KT-95, SK-9709 (Try-D-Ala-Phe-Leu-Arg (CH$_2$NH) Arg-NH$_2$), TAN-684, E-2078, EMD-60400 (N-methyl-N((1S))-1-phenyl-2-((3S)-3-hydroxypyrrolidin-1-yl)-ethyl-2-aminophenylacetamide), FE-200041, FE-200665, FE-200666, PD-117302, PD-129290, RP-61127, SB-215519, SB-215520, SEP-130551, XE-440, ZT-52537, ZT-52656A, Nalfurafine, OHM-3295, Apadoline ((+)-10-[(1R)-methyl-2-(1-pyrrolidinyl)ethyl]-N-propylphenothiazine-2-carboxamide), Tifluadom, TRK-820 ((−)-17-(cyclopropylmethyl)-3,14β-dihydroxy-4,5α-epoxy-6β-[N-methyl-trans-3-(3-furyl)acrylamide]morphinane hydrochloride), HZ-2, Butorphanol, Gosha-Jinki-gan, J-8970, MR-1268, N-CBM-TAMO, CL-891601 and the like. U-50488, Asimadoline and Spiradoline are preferable.

In the invention, the "salts" are not particularly limited so long as they are pharmaceutically acceptable salts. Examples of salts are salts with inorganic acids such as hydrochloric acid, hydrobromic acid, hydroiodic acid, nitric acid, sulfuric acid and phosphoric acid, salts with organic acids such as acetic acid, fumaric acid, maleic acid, succinic acid, citric acid, tartaric acid, adipic acid, lactic acid, methanesulfonic acid, trifluoromethanesulfonic acid and p-toluenesulfonic acid, salts with alkali metals such as lithium, sodium and potassium, salts with alkaline earth metals such as calcium and magnesium, quaternary salts with ammonia and methyl iodide, and the like. When the compounds represented by the above-mentioned general formula, the compounds having the structure of arylacetic acid (N-alkyl-N-(N',N'-dialkyl)aminoalkyl)amide and the like have geometric isomers or optical isomers, these isomers are also included in the scope of the present invention, and these compounds can be in the form of hydrates or solvates.

The κ-opioid receptor agonist of the invention can be administered either orally or parenterally. Examples of the dosage form include tablets, capsules, granules, powders, injection solutions, eye drops and the like. These can be prepared by techniques which have been widely used.

For example, oral preparations such as tablets, capsules, granules and powders can be prepared using, as required, excipients such as lactose, mannitol, starch, crystalline cellulose, light anhydrous silicic acid, calcium carbonate and calcium hydrogenphosphate, lubricants such as stearic acid, magnesium stearate and talc, binders such as starch, hydroxypropylcellulose, hydroxypropylmethylcellulose and polyvinyl pyrrolidone, disintegrants such as carboxymethylcellulose, low-substituted hydroxypropylcellulose and calcium citrate, coating agents such as hydroxypropylmethylcellulose, macrogol and silicone resin, stabilizers such as ethyl p-oxybenzoate and benzyl alcohol, corrigents such as sweetening agents, sour agents and flavors, and the like.

Parenteral preparations such as injection solutions and eye drops can be prepared using, as required, tonicity agents such as sodium chloride and conc. glycerin, buffers such as sodium phosphate and sodium acetate, surfactants such as polyoxyethylenesorbitan monooleate, polyoxy 40 stearate and polyoxyethylene hydrogenated castor oil, stabilizers such as sodium citrate and sodium edetate, preservatives such as benzalkonium chloride and paraben, and the like.

The invention also relates to a method for treating pain, especially chronic pain, which comprises administering the inhibitor of pain threshold decrease to a patient at a therapeutically effective dose.

The dose of the κ-opioid receptor agonist can properly be selected depending on the condition of a disease, the age of a patient, the dosage form and the like. For example, an oral preparation can be administered at a dose of, usually from 0.1 to 5,000 mg, preferably from 1 to 1,000 mg per day either once or in several portions.

The invention further relates to use of a κ-opioid receptor agonist for production of the inhibitor of pain threshold decrease.

As is apparent from the results of a test for inhibition of pain threshold decrease by a repetitive cold stress which will be described later, when the κ-opioid receptor agonist is continuously administered, the decrease in pain threshold in the repetitive cold stress can effectively be inhibited. Accordingly, the κ-opioid receptor agonist is useful as an inhibitor of pain threshold decrease, and is effective for treating chronic pain caused by the decrease in pain threshold in particular.

BEST MODE FOR CARRYING OUT THE INVENTION

Figure 1:
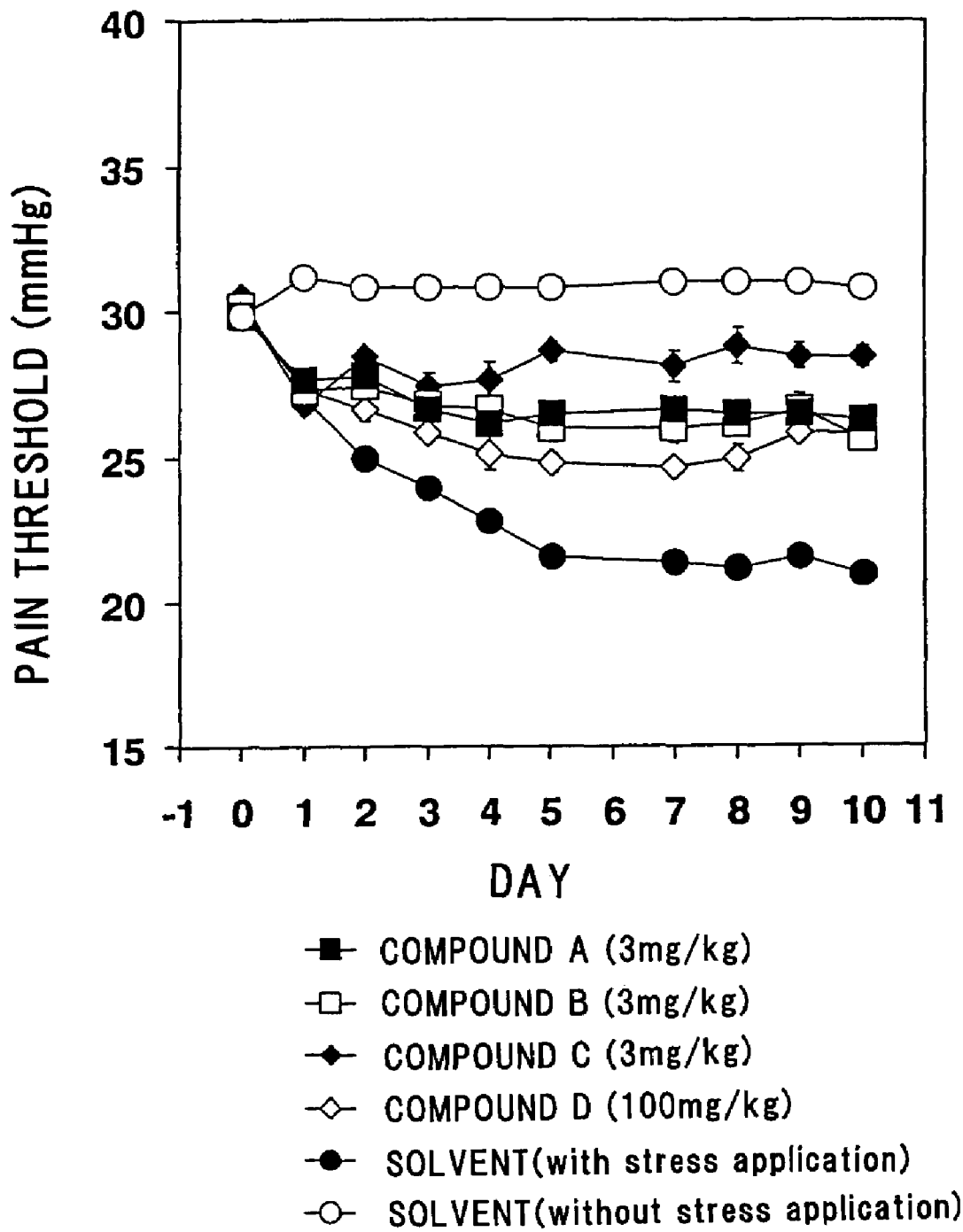
FIG. 1 is a graph showing a change with time of a pain threshold (mmHg) in repetitive cold stress rat models when using test compounds.

Examples of the invention are described below. However, these are for understanding the invention well, and are not to limit the scope of the invention.

[Pharmacological Test]

1. Test for Inhibition of Pain Threshold Decrease by Repetitive Cold Stress (Continuous Administration)

It is reported in Int Acad Biomed Drug Res. 11:277-280 (1996) by Hata T. et al. that a pain threshold is decreased by applying a repetitive cold stress to experimental animals. Accordingly, repetitive cold stress models were prepared according to the method described in the foregoing document, and an activity of each test compound on a decrease in pain threshold was evaluated.

(Preparation of Repetitive Cold Stress Models)

Everyday in the daytime (from 11:00 A.M. to 6:00 P.M.), the position of rats was changed between a breeding room maintained at room temperature (23° C.) and a cage put in a cold room set at −3° C. every one hour. From evening to morning (from 6:00 P.M. to 9:00 A.M.), rats were bred in a cold room maintained at −3° C.

(Pain Threshold Measurement: Randall-Selitto Method)

A pain threshold was measured according to a paw pressure pain method (Randall-Selitto method) that Randall L. O. et al. have reported in Arch. Int. Pharmacodyn. Ther., 111, 409-419 (1957). That is, the right hind paw was gradually pressed with a pressure stimulation analgesic effect device, and a pressure when showing a squeaking reaction or an escaping reaction was defined as a pain threshold (mmHg).

(Preparation of a Test Compound Solution)

The following compounds were used as a κ-opioid receptor agonist;

(+)-3-acetyl-6-chloro-2-[2-(3-(N-(2-hydroxyethyl)-N-isopropylamino)propoxy)-5-methoxyphenyl]benzothiazoline hydrochloride (compound A), (+)-3-acetyl-6-chloro-2-[2-(3-(N-(2-methoxyethyl)-N-isopropylamino)propoxy)-5-methoxyphenyl]benzothiazolinediacetyl tartrate (compound B), (+)-3-acetyl-6-chloro-2-[2-(3-(N-(2-ethoxyethyl)-N-isopropylamino)propoxy)-5-methoxyphenyl]benzothiazolinediacetyl tartrate (compound C), 2,2-diphenyl-N-[2-(3-(S)-hydroxy-1-pyrrolidinyl)-1-(S)-phenylethyl]methylacetamide hydrochloride (compound D), trans-2-(3,4-dichlorophenyl)-N-methyl-N-[2-(1-pyrrolidinyl)cyclohexyl]acetamide methanesulfonate (compound E), (+)-3-acetyl-6-chloro-2-[2-(3-chloropropoxy)-5-methoxyphenyl]benzothiazoline hydrochloride (compound F), 3-acetyl-6-chloro-2-[2-(3-(N-(2-hydroxyethyl)-N-isopropylamino)-1-methylpropoxy)-5-methoxyphenyl]benzothiazoline hydrochloride (compound G), (+)-2-[2-(3-(N-(2-acetoxyethyl)-N-isopropylamino)propoxy)-5-methoxyphenyl]-3-acetyl-6-chlorobenzothiazoline hydrochloride (compound H), (+)-3-acetyl-6-chloro-2-[2-(3-(N-isopropyl-(N-methoxymethyloxyethyl)amino)propoxy)-5-methoxyphenyl]benzothiazoline hydrochloride (compound I),
2-(3,4-dichlorophenyl)-N-methyl-N-[(5R*,7S*,8S*)-7-(1-pyrrolidinyl)-1-oxaspiro[4,5]deca-8-yl]acetamide methanesulfonate (compound J) and
3-acetyl-6-chloro-2-[2-(3-(N-(2-ethoxyethyl)-N-isopropylamino)propoxy)-5-methoxyphenyl]benzothiazolinediacetyl hydrochloride (compound K).

Diclofenac (compound L), a typical compound of a non-steroidal antiinflammatory and analgesic drug, was used as a comparative compound. Each test compound was dissolved in a 1% methylcellulose solution or a 0.9% physiological saline solution to prepare a test compound solution such that a dose was 5 mL per kg of the body weight.

As a control, 1% methylcellulose (solvent alone) was used in an oral administration test, and a 0.9% physiological saline solution was used in a subcutaneous administration test.

(Route of Administration and Dose of a Test Compound)

Compounds A, B, C, F, G, H and I were orally administered at a dose of 3 mg/kg, compound D at a dose of 100 mg/kg, and compound K at a dose of 10 mg/kg respectively. Compounds E and J were subcutaneously administered at a dose of 3 mg/kg.

(Test Method)

The test compound solution was subjected to intragastric forced oral administration or dorsal subcutaneous administration once a day from the day when the repetitive cold stress was applied. A pain threshold was measured according to the Randall-Selitto method everyday from the day when the stress was applied after rats were bred in an atmosphere of room temperature for approximately 2 hours and before administering the next test compound.

FIG. 1 shows a change with time (day 1 after administration of the test compound) of the pain threshold (mmHg) in repetitive cold stress rat models when using each test compound (each of compounds A to D). Table 1 shows a rate of inhibition of pain threshold decrease of each test compound on day 8 after applying the repetitive cold stress when using each test compound (each of compounds A to L). The rate of inhibition of pain threshold decrease (%) was calculated by the following formula using a pain threshold of a solvent administration group as a standard. In FIG. 1 and Table 1, the pain threshold and the rate of inhibition of pain threshold decrease are shown in terms of an average value of 5 or 6 cases.

Rate of inhibition of pain threshold decrease (%)={1-(pain threshold of solvent administration group 2—pain threshold of test compound administration group)/(pain threshold of solvent administration group 2—pain threshold of solvent administration group 1)}×100

TABLE 1

| | Test compound | Stress application | Rate of inhibition of pain threshold decrease (%) |
|---|---|---|---|
| Example 1 | Compound A | with | 52.1 |
| Example 2 | Compound B | with | 53.9 |
| Example 3 | Compound C | with | 73.4 |
| Example 4 | Compound D | with | 45.0 |
| Example 5 | Compound E | with | 59.6 |
| Example 6 | Compound F | with | 43.1 |
| Example 7 | Compound G | with | 32.8 |
| Example 8 | Compound H | with | 34.5 |
| Example 9 | Compound I | with | 43.1 |
| Example 10 | Compound J | with | 40.4 |
| Example 11 | Compound K | with | 62.7 |
| Comparative Example 1 | Compound L | with | 2.0 |
| Solvent administration group 1 | — | with | 0.0 |
| Solvent administration group 2 | — | without | 100.0 |

(Test Results)

As is apparent from FIG. 1, in solvent administration group 1 (with stress application), when the repetitive cold stress was applied to rats, the notable decrease in pain threshold was observed for five days after stress application followed by flat state. As is clear from Table 1, the κ-opioid receptor agonists (Examples 1 to 11) inhibit the decrease in pain threshold, whereas with diclofenac (Comparative Example 1), a non-steroidal antiinflammatory drug, an activity on inhibiting a pain threshold was not observed at all. The rate of inhibition of pain threshold decrease in the κ-opioid receptor agonists (Examples 1 to 11) was from 33 to 73%, whereas an activity on inhibiting a decrease in pain threshold was not observed at all in diclofenac.

2. Test for Inhibition of Pain Threshold decrease by Repetitive Cold Stress (Single Administration)

The test was conducted in the same manner as the foregoing "1. Test for inhibition of pain threshold decrease by repetitive cold stress (continuous administration)" except that each test compound (each of compounds A to D) was administered once after 8 days from the day when the repetitive cold stress was applied, and a pain threshold after 24 hours from the administration of each test compound was measured.

Table 2 shows a pain threshold (mmHg) and a rate of inhibition of pain threshold decrease when 24 hours elapsed after administering each test compound on day 8 from applying of the repetitive cold stress. The pain threshold and the rate of inhibition of pain threshold decrease in Table 2 are shown in terms of an average value of 6 cases.

Table 2

| | Test compound | Stress application | Pain threshold (mmHg) | Rate of inhibition of pain threshold decrease (%) |
|---|---|---|---|---|
| Example 12 | Compound A | with | 21.7 | 0 |
| Example 13 | Compound B | with | 21.5 | −1.9 |
| Example 14 | Compound C | with | 21.7 | 0 |
| Example 15 | Compound D | with | 21.5 | −1.9 |
| Solvent administration group 3 | — | with | 21.7 | 0 |
| Solvent administration group 4 | — | without | 30.7 | 100 |

(Test Results)

As shown in Table 2, the decrease in pain threshold was clearly observed in rats with the stress applied for 8 days in comparison with rats without the stress application. When the κ-opioid receptor agonist was administered to rats with the stress applied, the pain threshold when 24 hours elapsed after administration was not found to be different from the pain threshold of the solvent administration group.

(Consideration)

From the results of the tests for inhibition of pain threshold decrease by the repetitive cold stress in the continuous administration and the single administration, it is found that the inhibitor of pain threshold decrease of the invention inhibits the decrease in pain threshold even when the drug disappears in the blood after the lapse of more than 24 hours from the administration. That is, the inhibitor of pain threshold decrease of the invention is not a symptom-therapeutic drug which exhibits an activity when present in the blood, but a drug which is characterized in that the pain threshold can be maintained over a long period of time by administration once a day. Accordingly, it can radically improve diseases with the decrease in pain threshold.

[Preparation Example]

A general preparation example of the inhibitor of pain threshold decrease in the invention is described below.

| 1) Tablets | |
| --- | --- |
| Formulation 1 | In 100 mg, |
| Compound A | 1 mg |
| Lactose | 66.4 mg |
| Cornstarch | 20 mg |
| Calcium carboxymethylcellulose | 6 mg |
| Hydroxypropylcellulose | 4 mg |
| Magnesium stearate | 0.6 mg |

The tablets of the foregoing formulation were coated with 2 mg of a coating agent (a usual coating agent such as hydroxypropylmethylcellulose, macrogol or a silicone resin) to obtain desired coated tablets. Desired tablets can be obtained by properly changing the amounts of compound A and additives.

| 2) Capsules | |
| --- | --- |
| Formulation 1 | In 150 mg, |
| Compound B | 5 mg |
| Lactose | 145 mg |

Desired capsules can be obtained by properly changing the mixing ratio of compound B and lactose.

INDUSTRIAL APPLICABILITY

The κ-opioid receptor agonist is useful as an inhibitor of pain threshold decrease, and is effective for treating chronic pain caused by the decrease in pain threshold in particular.

The invention claimed is:

1. A method for treating chronic pain comprising administering to a patient an effective amount of a κ-opioid receptor agonist which is a compound represented by the following formula or a pharmaceutically acceptable salt thereof:

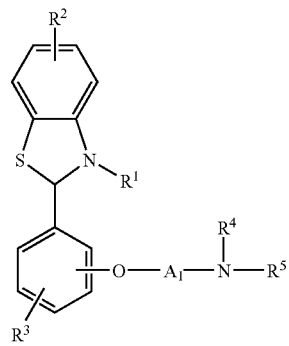

wherein $R^1$ represents an acyl group;

$R^2$ and $R^3$, which are the same or different, represent a hydrogen atom, a halogen atom, an alkyl group, a cycloalkyl group, an aryl group, a hydroxyl group or its ester, an alkoxy group, an aryloxy group, a carboxy group or its ester, an alkylcarbonyl group, an arylcarbonyl group, an amino group, an alkylamino group, an arylamino group, a cyano group or a nitro group, the alkyl group, the cycloalkyl group, the aryl group, the alkoxy group, the aryloxy group, the alkylcarbonyl group, the arylcarbonyl group, the alkylamino group or the arylamino group can be substituted with a halogen atom, an alkyl group, a cycloalkyl group, an aryl group, a hydroxyl group or its ester, an alkoxy group, an aryloxy group, a carboxy group or its ester, an alkylcarbonyl group, an arylcarbonyl group, an amino group, an alkylamino group, an arylamino group, a cyano group or a nitro group;

$R^4$ and $R^5$, which are the same or different, represent a hydrogen atom, an alkyl group, a cycloalkyl group, an aryl group, a hydroxyl group or its ester, an alkoxy group, an aryloxy group or an acyl group, the alkyl group, the cycloalkyl group, the aryl group, the alkoxy group, the aryloxy group or the acyl group can be substituted with a halogen atom, an alkyl group, a cycloalkyl group, an aryl group, a hydroxyl group or its ester, an alkoxy group, an aryloxy group, a carboxy group or its ester, an alkylcarbonyl group, an arylcarbonyl group, an amino group, an alkylamino group, an arylamino group, a mercapto group, an alkylthio group, an arylthio group, a cyano group, a nitro group or a heterocycle, and further the alkyl group, the cycloalkyl group, the aryl group, the alkoxy group, the aryloxy group, the alkylcarbonyl group, the arylcarbonyl group, the alkylamino group, the arylamino group, the alkylthio group, the arylthio group or the heterocycle can be substituted with an aryl group, a hydroxyl group or its ester, an alkoxy group, an aryloxy group, an alkoxyalkoxy group, a carboxy group or its ester;

$R^4$ and $R^5$ can be bound to form a heterocycle, the heterocycle can be substituted with a halogen atom, an alkyl group, a cycloalkyl group, an aryl group, a hydroxyl group or its ester, an alkoxy group, an aryloxy group, a carboxy group or its ester, and further the alkyl group, the cycloalkyl group, the aryl group, the alkoxy group or the aryloxy group can be substituted with an aryl group, a hydroxyl group or its ester, an alkoxy group, an aryloxy group, an alkoxyalkoxy group, a carboxy group or its ester; and $A_1$ represents an alkylene group.

2. The method as claimed in claim 1, wherein the κ-opioid receptor agonist is selected from the group consisting of (+)-3-acetyl-6-chloro-2-[2-(3-(N-(2-hydroxyethyl)-N-isopropylamino)propoxy)-5-methoxyphenyl]benzothiazoline, (+)-3-acetyl-6-chloro-2-[2-(3-(N-(2-methoxyethyl)-N-isopropylamino)propoxy)-5-methoxyphenyl]benzothiazoline, (+)-3-acetyl-6-chloro-2-[2-(3-(N-(2-ethoxyethyl)-N-isopropylamino)propoxy)-5-methoxyphenyl]benzothiazoline, (+)-3-acetyl-6-chloro-2-[2-(3-chloropropoxy)-5-methoxyphenyl]benzothiazoline, 3-acetyl-6-chloro-2-[2-(3-(N-(2-hydroxyethyl)-N-isopropylamino)-1-methylpropoxy)-5-methoxyphenyl]benzothiazoline, (+)-2-[2-(3-(N-(2-acetoxyethyl)-N-isopropylamino)propoxy)-5-methoxyphenyl]-3-acetyl-6-chlorobenzothiazoline, (+)-3-acetyl-6-chloro-2-[2-(3-(N-isopropyl-(N-methoxymethyloxyethyl)amino)propoxy)-5-methoxyphenyl]benzothiazoline and 3-acetyl-6-chloro-2-[2-(3-(N-(2-ethoxyethyl)-N-isopropylamino)propoxy)-5-methoxyphenyl]benzothiazoline, or a pharmaceutically acceptable salt thereof.

3. The method as claimed in claim 1, wherein the κ-opioid receptor agonist is continuously administered.

4. The method as claimed in claim 1, wherein the κ-opioid receptor agonist is (+)-3-acetyl-6-chloro-2-[2-(3-(N-(2-hydroxyethyl)-N-isopropylamino)propoxy)-5-methoxyphenyl]benzothiazoline.

5. The method as claimed in claim 1, wherein the κ-opioid receptor agonist is (+)-3-acetyl-6-chloro-2-[2-(3-(N-(2-methoxyethyl)-N-isopropylamino)propoxy)-5-methoxyphenyl]benzothiazoline.

6. The method as claimed in claim 1, wherein the κ-opioid receptor agonist is (+)-3-acetyl-6-chloro-2-[2-(3-(N-(2-ethoxyethyl)-N-isopropylamino)propoxy)-5-methoxyphenyl]benzothiazoline.

7. The method as claimed in claim 1, wherein the κ-opioid receptor agonist is 3-acetyl-6-chloro-2-[2-(3-(N-(2-ethoxyethyl)-N-isopropylamino)propoxy)-5-methoxyphenyl]benzothiazoline.

\* \* \* \* \*